United States Patent [19]

Di Mino

[11] Patent Number: 4,667,677

[45] Date of Patent: May 26, 1987

[54] CORONA DISCHARGE THERMOTHERAPY TECHNIQUE

[75] Inventor: Alfonso Di Mino, Woodcliff Lake, N.J.

[73] Assignee: ADM Tronics Unlimited, Inc., Northvale, N.J.

[21] Appl. No.: 856,182

[22] Filed: Apr. 28, 1986

[51] Int. Cl.⁴ .............................................. A61N 1/02
[52] U.S. Cl. ................................ 128/419 R; 128/399; 128/783; 128/800
[58] Field of Search ........... 128/783, 800, 804, 419 R, 128/419 N, 420 R, 421, 422, 423 R, 362, 399; 361/232

[56] References Cited

U.S. PATENT DOCUMENTS

| 3,563,246 | 2/1971 | Puharich et al. | 128/422 |
| 4,572,194 | 2/1986 | Head | 128/419 R |

FOREIGN PATENT DOCUMENTS

| 2907013 | 8/1979 | Fed. Rep. of Germany | 128/421 |
| 1156153 | 6/1969 | United Kingdom | 128/419 N |
| 266086 | 7/1970 | U.S.S.R. | 128/419 R |

*Primary Examiner*—Lee S. Cohen
*Attorney, Agent, or Firm*—Michael Ebert

[57] ABSTRACT

A non-invasive thermotherapy technique for relieving pain and obtaining other beneficial effects. In this technique, the skin surface of a patient overlying a problem region such as an arthritic joint is scanned by a corona discharge beam emanating from a discharge electrode to which is applied periodic bursts of radio-frequency energy whose repetition rate is at a sonic frequency and whose peak amplitude is such as to cause a corona discharge. This energy is derived from a radio-frequency carrier generator whose operating frequency is preferably in the range of 100 to 300 KHz. This carrier is overmodulated in amplitude at a sonic rate, whose frequency is preferably in the 3000 to 5000 Hz range, so that the carrier is interrupted periodically to produce the bursts.

7 Claims, 4 Drawing Figures

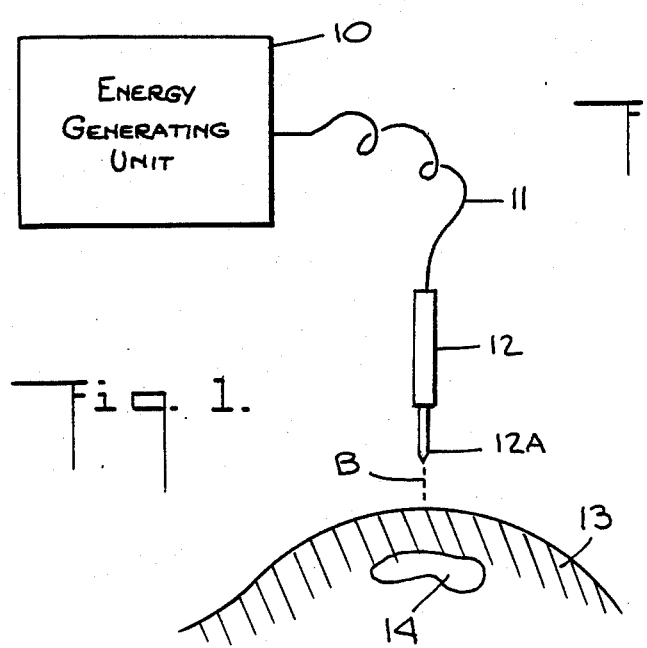
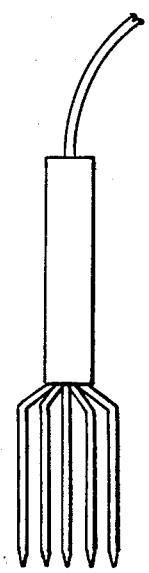
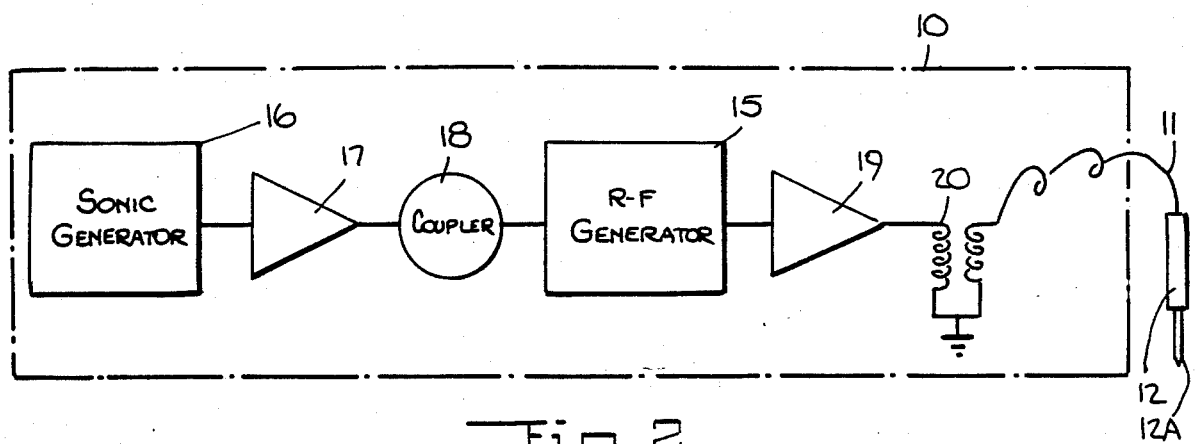
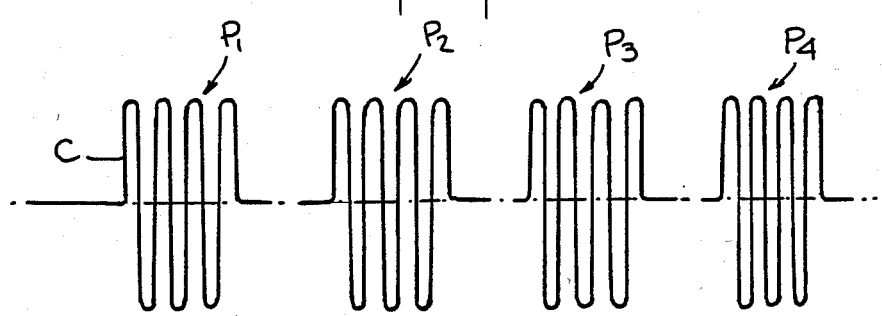

CORONA DISCHARGE THERMOTHERAPY TECHNIQUE

BACKGROUND OF INVENTION

1. Field of Invention:

This invention relates generally to thermotherapy, and in particular to a non-invasive technique for relieving pain and obtaining other salutary effects in which the skin surface of a patient overlying a problem region is subjected to a corona discharge beam derived by periodic bursts of radio frequency energy whose repetition rate is at a sonic frequency.

2. Status of Prior Art:

The term "problem region" as used herein refers to a set of muscles, an arthritic joint or any other site underlying the skin of a patient which is causing difficulty and which lends itself to treatment by thermotherapy.

The interior of the human body has a normal temperature level which is usually said to be 98.6° F. But actually, in the course of each 24-hour period, the body temperature rises above or falls somewhat below this nominal value. Body temperature is determined by the relationship existing between the amount of heat internally generated, which depends on basal metabolism and the amount of heat escaping from the body. Additional heat is produced as a result of muscular activity, this being dissipated by an increase in radiation, conduction or evaporation from the skin surface and by more rapid and deep breathing. If the heat produced by the body surpasses heat losses therefrom, this gives rise to fever.

Medical practitioners since ancient times have known that the application of heat to the body is useful in the relief of muscle soreness and various aches and pains, as well as in the treatment of certain pathological conditions. Thus the use of heat for the treatment of arthritis and other abnormalities is now commonplace. Hot water bottles and electrical heating pads are in widespread use, not merely to provide warmth, but also to afford a degree of relief or therapy for various conditions. In applying heat to the surface of the body, one may do so by convection, by direct contact with a warmed substance; that is, by conduction, or by radiating energy into the body.

As pointed out in chapter 10, "Therapeutic Heat" in the text *Therapeutic Heat and Cold,* edited by Justus F. Lehmann and published in 1982 by Williams and Wilkins, it is generally accepted that heat produces desirable therapeutic effects, for it increases the extensibility of collagen tissues, it decreases joint stiffness, and it affords pain relief. Moreover, heat relieves muscular spasms, it aids in the resolution of inflammatory infiltrates, edema and exudates, and it enhances blood flow.

The exact physiological mechanisms by which applied heat creates soothing and analgesic effects are not known. However, regardless of how heat is generated, the result within the heated tissue is essentially the same, for heat produces a rise in the temperature of the tissue with a concomitant increase in metabolism. As a consequence, there is a relative increase in the accumulation of metabolic wastes such as carbon dioxide and acid metabolites. And because heat acts as a vasodilator, this dilation results in increased local circulation and leads to improved cellular nutrition and to an enhanced exchange of wastes. Further benefits are obtained because a greater number of phagocytes and antibodies are carried by the blood into the region being heated.

A technique in accordance with the invention makes use of conversive heating which involves the transformation of some other form of energy into heat. The most commonly used sources of such energy are radio waves in the short wave and microwave bands of the electromagnetic wave spectrum, and ultrasonic energy. Shortwave diathermy uses radio waves in the 10 to 100 MHz frequency range, the human tissues being treated with high-frequency current, either by way of induction or conduction. In microwave diathermy, the frequency is usually about 2500 MHz. While shortwave diathermy tends to spread widely in the body tissues, microwaves are quasi-optical and can be focused and directed for the heating of small selective areas.

Ultrasonic therapy employs high-frequency sound waves, but this energy is selective in its heating properties. Because ultrasonic energy is reflective at interfaces in the body, in excessive dosages it may be destructive.

The present invention involves a therapeutic technique in which a corona discharge beam is created by applying to a discharge electrode bursts of radio-frequency energy whose repetition rate is at a sonic frequency. Hence of background interest are the Di Mino Pat. Nos. 3,676,633 and 3,617,684, in which a corona discharge beam is applied to a resistor in a printed circuit so as to change the ohmic value thereof. These patents, however, have nothing to do with thermotherapy.

Also of background interest is the Hance et al. U.S. Pat. No. 4,368,410, which discloses an ultrasound therapy technique in which the ultrasound energy is pulsed. In the Kuris et al. U.S. Pat. No. 3,980,906, ultrasonic energy modulated at a sonic rate is applied to a vibrating toothbrush or razor. And in Indeck, U.S. Pat. No. 4,343,301, non-invasive neurosurgery is performed using two ultrasonic beams to create a low frequency beat pattern.

Also in the field of ultrasonic therapy, we find the U.S. Pat. Nos. to Kofsky et al., 4,177,819; Nemic, 4,153,061; and Griffith, Jr., 3,096,768.

SUMMARY OF INVENTION

In view of the foregoing, the main object of this invention is to provide a thermotherapy technique for relieving pain and obtaining other beneficial effects by subjecting the skin of a patient in an area overlying a problem region with a corona discharge beam derived from a low radio-frequency power source, the corona discharge beam having no adverse effects on the patient.

The term "low radio-frequency" as used herein refers to that band in the radio frequency spectrum which lies in the 100,000 to 1,000,000 Hz frequency range normally used for long distance communication. This low radio-frequency band is largely reserved for radio telegraphy, but has not heretofore been used in diathermy.

More particularly, an object of this invention is to provide a technique of the above-type in which the radio-frequency power for producing the corona discharge beam is generated in periodic bursts whose repetition rate is at a sonic frequency.

Briefly stated, in a thermotherapy technique in accordance with the invention, use is made of a discharge electrode probe which can be manipulated to scan any skin area of a patient overlying a problem region. A corona discharge beam is projected from the tip of the electrode and impinges on the skin to be absorbed by the underlying tissue of the patient and converted into therapeutic heat.

The corona discharge beam is derived from an energy generating unit in which a low radio-frequency carrier of relatively low power is overmodulated by a sonic frequency signal to create periodic bursts of radio-frequency energy whose repetition rate is at the sonic frequency and whose peak amplitude is such as to cause a corona discharge.

OUTLINE OF DRAWINGS

For a better understanding of the invention as well as other objects and further features thereof, reference is made to the following detailed description to be read in conjunction with the accompanying drawings, wherein:

FIG. 1 illustrates the basic components of the system used in practicing a thermotherapy technique in accordance with the invention;

FIG. 2 is a block diagram showing the various stages of the energy-generating unit included in the system;

FIG. 3 illustrates the waveform of the power applied to the discharge electrode included in the system; and FIG. 4 shows an alternative form of probe having multiple electrodes.

DESCRIPTION OF INVENTION

1. The Basic Technique:

Referring now to FIG. 1, a technique in accordance with the invention makes use of an energy-generating unit 10 which yields periodic bursts of radio-frequency energy whose repetition rate is at a sonic frequency. This energy is applied via a flexible wire 11 to a hand-held probe 12 having a pointed discharge electrode 12A from which is projected a corona discharge beam B. Beach B is directed toward and impinges on the skin surface 13 of a patient that overlies a problem region 14.

The tip of electrode 12A is placed within a few centimeters of the skin, the distance between the tip and the skin being such that the corona discharge beam impinges on the skin to be absorbed by the underlying tissue of the patient and converted into therapeutic heat. The zone of impingement, because of the corona discharge beam, is small, and in order to irradiate a relatively large skin area, the beam is scanned over this area so that the entire problem region therebelow is subjected to treatment.

A corona discharge is a highly active glow region surrounding a discharge electrode. When the electrode is a pointed wire as in the present case, this glow region extends a short distance beyond this point. Assuming the wire is negatively charged, the free electrons in the air in the region of the intense electric field surrounding the wire gains energy in this field to produce positive ions and other electrons by collision. In turn, these new electrons are accelerated and produce further ionization. This cumulative process results in an electronic avalanche in which the positive ions are accelerated toward and bombard the charged wire. As a consequence of such ionic bombardment, secondary electrons are ejected from the wire surface which act to sustain the corona discharge.

When the voltage applied to the discharge electrode is elevated to a level exceeding the point at which a stable corona discharge is maintained, the air dielectric then completely breaks down to cause a spark discharge. In order to produce a corona discharge, the peak voltage on the discharge electrode must be relatively high but below the level resulting in a spark discharge.

The continuous application of a low radio-frequency energy of relatively low power will not result in a corona discharge. But because in the energy-generating unit 10, the continuous radio-frequency carrier is produced in bursts which shock excite a tank coil included in the system, the resultant energy surges have a peak amplitude sufficient to produce a sustained corona discharge beam.

2. The Energy Generating Unit:

Referring now to FIG. 2, the energy generating unit 10 includes a low radio-frequency generator 15 producing a carrier lying in the frequency range of 200,000 to 300,000 Hz. In practice, this generator is frequency controlled by a piezoelectric crystal oscillator operating at, say, 200 KHz, the carrier generator also being stabilized as to amplitude. A conventional low radio-frequency generator may be used for this purpose.

Also included in the unit is an audio-frequency generator 16 operating in the frequency range of 3000 to 5000 Hz to produce a sonic signal. This is amplified in amplifier 17 and applied to a coupler 18 which is so connected to radio-frequency generator 15 to effect amplitude modulation of the R-F carrier. Audio oscillator 16 is preferably a shielded, solid-state, transistorized generator which yields a steady monovalent signal with tolerances as minimal as present standards will allow. Amplifier 17 is also transistorized.

In amplitude-modulation, the amplitude of the radio-frequency carrier is varied in accordance with the signal, the resultant modulated wave containing side bands that are the sum and difference of the carrier and signal frequencies. If the modulation index "M" is zero, no signal information is conveyed to the carrier. Where, however, M=1 (100% modulation), then in the case of a sinusoidal carrier wave, the envelope of the carrier varies from zero to twice the value of its unmodulated amplitude. But if "M" exceeds unity, the carrier is then overmodulated, as a consequence of which the carrier is periodically interrupted at a repetition rate in accordance with the audio-frequency signal.

In the present invention, as shown in FIG. 3, the radio-frequency carrier C is overmodulated by the sonic frequency signal, this resulting in periodic bursts $P_1$, $P_2$, $P_3$, etc. of radio-frequency energy whose repetition rate is at the sonic frequency. These bursts of energy from R-F generator 15 are applied through an output amplifier 19 to a tank coil 20. Coil 20 is inductively coupled to an output coil connected by flexible lead 11 to probe 12.

Because tank coil 20 is shock excited by the bursts $P_1$, $P_2$ etc. of the radio-frequency energy, the resultant damped wave surges in coil 20 have a high peak amplitude, and this causes the desired corona discharge to produce a pencil beam which is both visible and audible. The reason it is visible is that the corona beam produces a blue glow, and the reason it is audible is that the bursts of energy are at a sonic rate and can therefore be heard. In practice, the power output of the system may be in the order of 5 to 15 watts. This level is far below any level that would result in burning or injury to a patient.

We have found that the resultant heat energy induced in a painful region of the human body is capable in a matter of 20 seconds of relieving this pain. We have also found that continued exposure of the problem region for a period of 30 to 40/seconds to the corona charge beam, in the case of inflammation due to a rheumatoid arthritis condition, will minimize the swelling, and that a marked reduction in swelling will be experienced about 24 hours after such exposure.

While there has been shown and described a preferred embodiment of a corona discharge thermotherapy technique in accordance with the invention, it will be appreciated that many changes and modifications may be made therein without, however, departing from the essential spirit thereof.

I claim:

1. A non-invasive thermotherapy technique for relieving pain in a problem region of the human body and obtaining salutary effects, said technique comprising the steps of:
    A. continuously generating a radio-frequency carrier;
    B. overmodulating said carrier with a sonic frequency signal to produce periodic bursts of radio-frequency energy whose repetition rate is determined by the sonic frequency;
    C. applying said bursts to a discharge electrode to produce a corona discharge beam; and
    D. directing said beam to impinge on the skin surface of a patient overlying the problem region.

2. A technique as set forth in claim 1, wherein said carrier is in the low-frequency radio range.

3. A technique as set forth in claim 2, wherein said carrier frequency is about 200,000 Hz.

4. A technique as set forth in claim 1, wherein said sonic frequency lies in the range of 3000 to 5000 Hz.

5. A technique as set forth in claim 1, wherein said radio-frequency carrier is produced by generating a carrier whose power is about 10 watts.

6. A technique as set forth in claim 1, wherein said bursts are applied to an electrode which is a pointed wire to create a single corona discharge beam.

7. A technique as set forth in claim 1, wherein said bursts are applied to an electrode constituted by a cluster of pointed wires to create multiple corona discharge beams.

* * * * *